United States Patent [19]

Takeuchi

[11] Patent Number: 4,966,151

[45] Date of Patent: Oct. 30, 1990

[54] ULTRASONIC DIAGNOSTIC APPARATUS

[75] Inventor: Yasuhito Takeuchi, Tokyo, Japan

[73] Assignee: Yokogawa Medical Systems Limited, Tokyo, Japan

[21] Appl. No.: 335,664

[22] PCT Filed: Sep. 30, 1987

[86] PCT No.: PCT/JP87/00713

§ 371 Date: Mar. 27, 1989

§ 102(e) Date: Mar. 27, 1989

[87] PCT Pub. No.: WO88/02240

PCT Pub. Date: Apr. 7, 1988

[30] Foreign Application Priority Data

Sep. 30, 1986 [JP] Japan .................................. 61-232647

[51] Int. Cl.$^5$ ............................................... A61B 8/12
[52] U.S. Cl. ............................ 128/660.05; 128/661.09
[58] Field of Search ...................... 128/661.07–661.10, 128/660.05, 662.04; 73/861.25

[56] References Cited

U.S. PATENT DOCUMENTS 4,431,936 2/1984 Fu et al. .................... 128/662.04 X
4,817,619 4/1989 Sugiyama et al. ............. 128/661.09

Primary Examiner—Francis Jaworski
Attorney, Agent, or Firm—Moonray Kojima

[57] ABSTRACT

In an ultrasonic diagnostic apparatus of this invention, the dimension of a sample volume can be adjusted both in the depth and azimuth directions in forming a transmission beam for both a B mode and a Doppler mode with the use of a common beam forming data, and an amount of radiation of the ultrasonic wave to a body to be examined can be reduced. In the B mode operation, transmission and reception of a sharply focusing ultrasonic beam are carried out based upon a B mode beam forming data, while in the Doppler mode, transmission and reception of a predetermined blurringly focusing ultrasonic beam are carried out based upon a beam forming data which is obtained by modifying the B mode beam forming data.

3 Claims, 5 Drawing Sheets

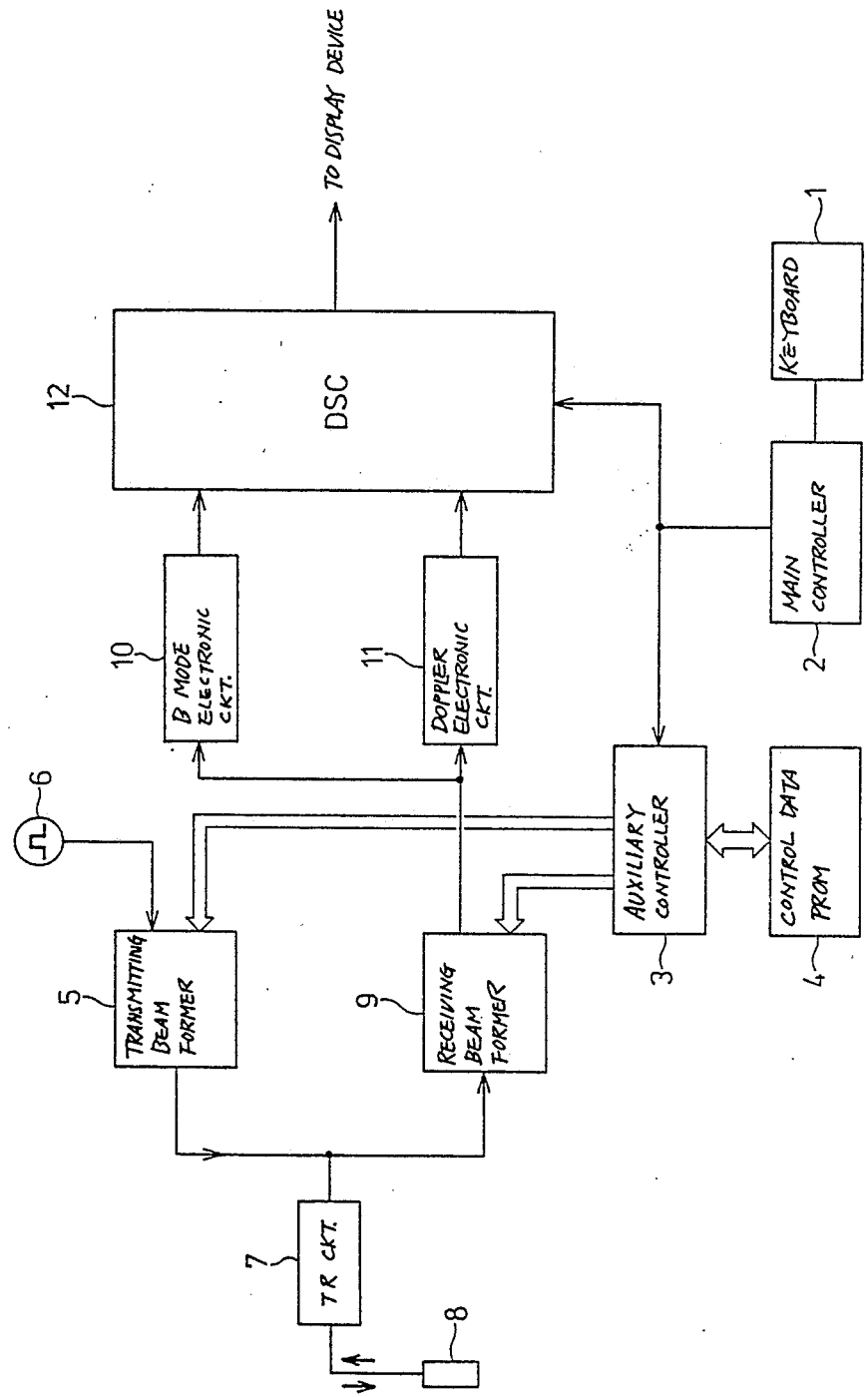

Fig.3A  Fig.3B  Fig.3C
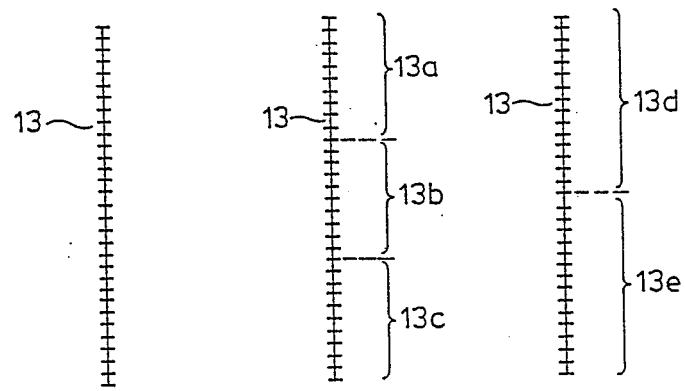
Fig.3D
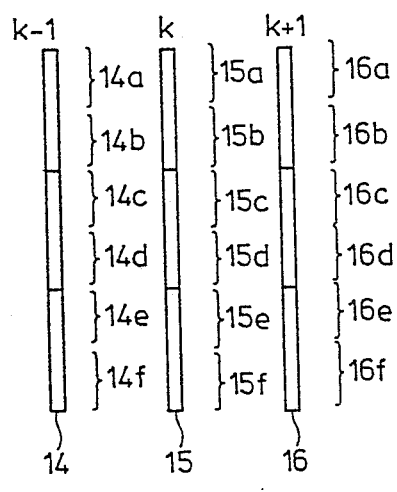
Fig.3E
| ELEMENT | SOUND-RAY NO. k-1 | SOUND-RAY NO. k-2 | --- |
|---|---|---|---|
| 0 | 1.926μs | 1.948μs | --- |
| 1 | 1.905μs | 1.933μs | --- |
| 2 | 1.885μs | | |
| 3 | | | |
| 4 | | | |
| ⋮ | | | |
| 32 | 0.000μs | 0.000μs | |
| ⋮ | | | |
| 59 | | | |
| 60 | | | |
| 61 | | | |
| 62 | | | |
| 63 | 1.234μs | 1.265μs | |
| 64 | 1.252μs | 1.289μs | |

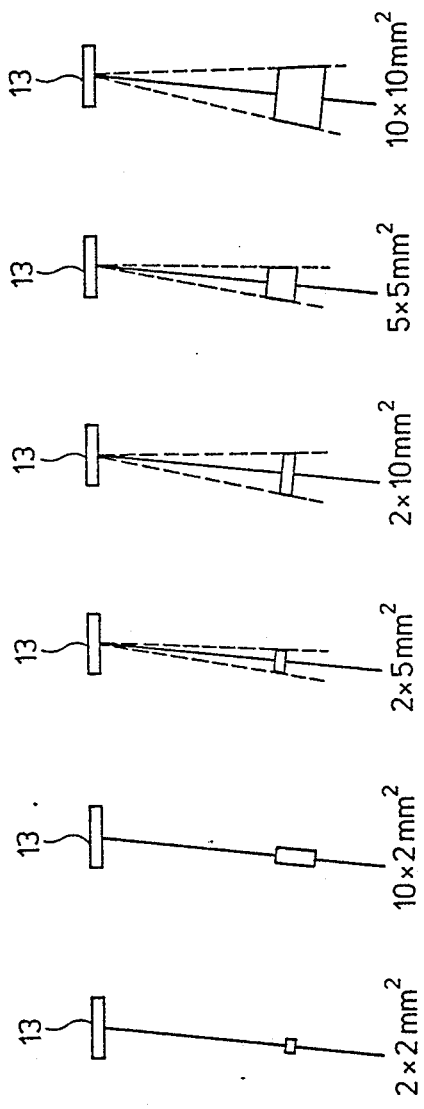

ULTRASONIC DIAGNOSTIC APPARATUS

TECHNICAL FIELD

The present invention relates to an improvement in an ultrasonic diagnostic apparatus provided with B mode and Doppler mode ultrasonic diagnostic functions, and more particularly to such a type of ultrasonic diagnostic apparatus in Which an improvement is made with respect to the configuratIon of the ultrasonic beam transmitted in the Doppler mode.

BACKGROUND ART

When an ultrasonic pulse is radiated toward a body to be examined, an echo returns from a reflection material inside of the body. Therefore, a tomographic image of the body under examination can be obtained if the strength of the echo is B mode displayed. Further, when the reflection material is motional, the frequency of the echo shifts from the transmission frequency due to a Doppler effect. By using this phenomenon, it is capable of knowing, for example, the direction and speed of a blood flowing in a heart or a blood vessel.

While the transmitting ultrasonic beam is required to have a sharpness to form a B mode image of excellent resolution, it is not necessarily required to have a sharpness in the Doppler mode, since in the latter mode utilized in an echo of a sample volume of a particular magnitude that is reflected from the body under examination. The magnitude of the sample volume is determined appropriately depending upon an object to be observed. An adjustment of the sample volume is carried out by adjusting the width of a range gate for use in receiving the echo. In the adjustment of the sample volume, the dimension of the sample volume in the depth direction increases as the width of the range gate is widened; however, the dimension in the direction perpendicular thereto, i.e. azimuth direction of the ultrasonic beam, cannot be changed, since it has been fixed in accordance with a profile of the ultrasonic beam. That is, there has heretofore been no freedom in setting the sample volume in the azimuth direction.

Recently, in the field of ultrasonic medical equipment, limitation regarding an amount of ultrasonic radiation has been strictly reduced. The pulse Doppler is a typical case &hat is liable to be contrary to the regulation concerning the amount of radiation, since due to the necessity for continuously observing a specific position, the ultrasonic beam of a particular sound-ray is transmitted and received at a maximum pulse repetitive frequency (PRF) allowable for the depth of the portion in question. In a conventional ultrasonic diagnostic apparatus provided with both the B mode and the Doppler mode diagnostic functions, a common beam forming data is used in forming the transmission beams for both the B mode and the Doppler mode, so that the ultrasonic beam radiated in the Doppler mode is as sharp as that in the B mode, thereby making it difficult to act upon the regulation.

DISCLOSURE OF THE INVENTION

An object of this invention is to provide an ultrasonic diagnostic apparatus in which in forming transmitting beams of both B mode and Doppler mode with the use of a common beam forming data, dimensional adjustments of a sample volume can be made in both depth and azimuth directions, and further an amount of radiation of the ultrasonic wave can be reduced.

In accordance with the invention, there is provided an ultrasonic diagnostic apparatus capable of transmitting and receiving an ultrasonic beam in both B mode and the Doppler mode which is characterized in that in the case of operating in the B mode, a sharply focusing ultrasonic beam is transmitted and received on the basis of the 8 mode beam forming data and in the case of operating in the Doppler mode, a predetermined blurringly focusing ultrasonic beam is transmitted and received on &he basis of a beam forming data that is a modification of the B mode beam forming data.

BRIEF DESCRIPTION OF THE DRAWINGS

FIG. 1 is a block diagram according to one embodiment of the present invention;

FIGS. 3A through 3E are diagrams for describing beam formings in the apparatus shown in FIG. 1;

FIGS. 5A through 5F are diagrams each showing a configuration of a sample volume formed in accordance with the embodiments of the present invention.

BEST MODE FOR CARRYING OUT THE INVENTION

Figure 2A:
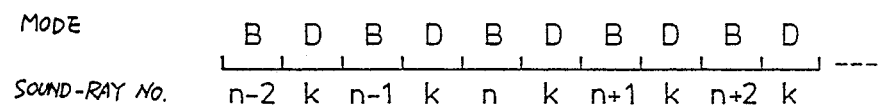
FIGS. 2A and 2B are diagrams each illustrating an allocation of sound-ray numbers in the apparatus shown in FIG. 1.

Hereinafter the present invention will be described in detail with reference to the accompanying drawings. FIG. 1 is a block diagram showing one embodiment of the present inventIon. In FIG. 1, reference numeral denotes a keyboard used for inputting an operation mode designating signal and a sound-ray number in a Doppler mode (hereinafter referred to as "D mode") to a main controller 2 by the operator's key manipulations. The main controller 2 outputs a control signal corresponding to the key manipulation. Reference numeral 3 denotes an auxiliary controller which in response to the control signal fed from the main controller 2, effects switchings between transmission and reception dependent upon the operation mode and controls the configuration of an ultrasonic beam with the use of data stored in a control data PROM (programmable read-only memory). Reference numeral 5 denotes a transmitting wave beam former which receives a timing signal for switching between the transmission and the reception from the auxiliary controller 3 and outputs a transmitting wave signal having a waveform dependent upon each of the modes in response to a trigger signal outputted from a transmitting wave trigger generator 6. Reference numeral 7 denotes a transmission/reception circuit (hereinafter referred to as "TR circuit") transmits a group of transmitting pulses subjected to delay distribution fed from the transmitting beam former 5 to the respective elements of a search unit 8 upon power amplification, and relays a group of receiving signals obtained from those elements to the receiving beam former 9 upon amplification. In response to a receiving beam control signal fed from the auxiliary controller 3, the receiving beam former 9 composes the group of the receiving signals from the TR circuit 7 to provide a single sound-ray receiving signal adapted to be processed in a B mode electronic circuit 10 and a Doppler electronic circuit 11. The B-mode electronic circuit 10 converts a B mode receiving signal to a digital signal upon processing the same, and the Doppler electronic circuit 11 converts a D mode receiving signal to a digital signal upon Doppler processing the same. Reference numeral 12 denotes a digital scan converter (hereinafter referred to as "DSC") for translating a format of an echo video signal to a format suitable for a standard television raster scan. The output of the DSC is displayed in a display device (not shown).

Figure 2B:
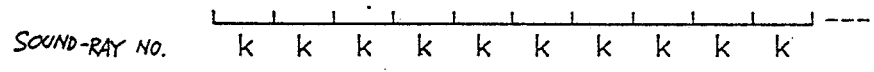

Next, description will be made with respect to the apparatus arranged as above By the key manipulation of the keyboard 1, either a combination mode of the B and D modes (hereinafter referred to as "B/D mode") or a sole D mode is designated, and the sound-ray number in the 0 mode is further designated, thereby operating the main controller 2. The main controller 2 inputs the control signal with the sound-ray number inclusive to both the auxiliary controller 3 and the DSC 12 in accordance with the input from the keyboard 1. In FIGS. 2A and 2B, there are shown assignments of the sound ray numbers. Here, the sound rays are so defined that they are arranged at an equi-interval in the order of the sound-ray number within the sound field to be scanned. FIG. 2A shows the assignment of the sound ray numbers in the case that the B/D mode is designated, in which the B mode and the D mode are alternately changed at every sound-ray. For the D mode, the k-th sound-ray as designated by the keyboard 1 is fixedly used, while for the B mode, the sound-ray is sequentially increased one by one from the first sound-ray. FIG. 2B shows the assignment of the sound ray numbers in the case of the sole D mode, in which the sound ray is fixed to the k-th one.

In order to direct the beam for one sound-ray under the B mode as is done normally, the control data for that sound-ray is applied as one set to both the transmitting beam former 5 and the receiving beam former 9 from the auxiliary controller 3 to thereby form the beam. Under the D mod ®, on the other hand, in order to enlarge (hereinafter referred to as "blur") the dimension of the sample volume in the azimuth direction of the ultrasonic beam, a part of the control data of the adjacent sound-raYs is given to every part of the opening of a vibrator array of the ultrasonic wave search unit 8. Such a blurring method is illustrated in FIG. 3A through 3E. In these figures, reference numeral 13 denotes the opening of &he vibrator array of the ultrasonic wave search unit 8 and 13a, 13b and 13c indicate the trisected parts of the opening 13, and 13d and 13e indicate the bisected parts thereof. Numerals 14, 18 and 16 indicate beam forming data to be applied to the opening 13. As a specific example, there is shown in FIG. 3E data set of delay amount that each element is to be imposed. Those data are for acute focusing to allow the B mode transmission and reception. More specifically, denoted by numerals 14, 15 and 16 are such beam forming data regarding the (k−1)−th, k−th, and (k+1)−th sound-rays, respectively. The beam forming data for each sound-ray is divided into six an characters a through f are added following those numerals. In those figures, FIG. 3A shows the beam forming for the B mode, in which the beam is focused to a maximum degree, FIG. 3B shows an example of the blurring for use in the D mode, and FIG. 3C shows another example of the blurring for use in the D mode. To the array opening 13 shown in FIG. 3A, applied is the sound ray beam forming data 15 (composed of 15a through 15f) shown in FIG. 3D, thereby forming the sound-ray focused to the maximum degree. In the array opening 13 in FIG. 3B, beam forming data of different sound-rays is applied to each of the trisected array opening parts. Specifically, the beam forming data 14a, 14b are applied to the trisected upper part opening 13a, the beam forming data 15c, 15d are applied to the trisected middle part opening 13b, and the beam forming data 16e, 16f are applied to the trisected lower part opening 13c. In this manner, by slightly displacing each of the focusing positions formed by the partial openings 13a, 13b and 13c in the upper, middle and lower parts of the array opening 13, the blurring is carried out. In the example of FIG. 3C, the array opening is bisected into two par&s 13d and 13e, in which the beam forming data 14a, 14b, 14c are applied to the array opening 13d, the beam forming data 15d, 15e, 15f are applied to the array opening 13e to thereby displace each of the focusing positions formed by the respective array openings and to thus carry out the blurring. In the above-described blurring, the trisected blurring in FIG. 3B (No. 1 blurring) forms a beam having a large sample volume dimension in the azimuth direction as compared with the bisected blurring in FIG. 3C (No. 2 blurring). The center point of the beam in the azimuth direction according to the No. I blurring is in coincidence with the direction of k. However, the center line of the azimuth angle according to the No. 2 blurring comes to the midpoint between k and (k−1). Although the beam forming data in the range of k±1 are used in the above-described embodiment, more expanded beam can be obtained if the number of division of the opening is increased to use data in the range of k±2.

As described, in carrying out the blurring, the opening is divided into a plural parts and certain beam forming data should be applied to each of the divided parts. Interleaving the beam forming data of the adjacent sound-rays with respect to each of the vibrator elements does not give an effect of the blurring, since although coincidence is made at the center, the phase delay occurs as the distance from the center increases and cancellation results in a certain position, thus a result is merely obtained such that the opening is in effect narrowed down. In addition, even if the average data incorporating the beam forming data of adjacent sound-rays is applied to the array opening 13, only a non-blurring beam is formed on a focusing point in a direction at the center of the directions toward which the sound-rays k and (k−1) are directed.

Figure 4:
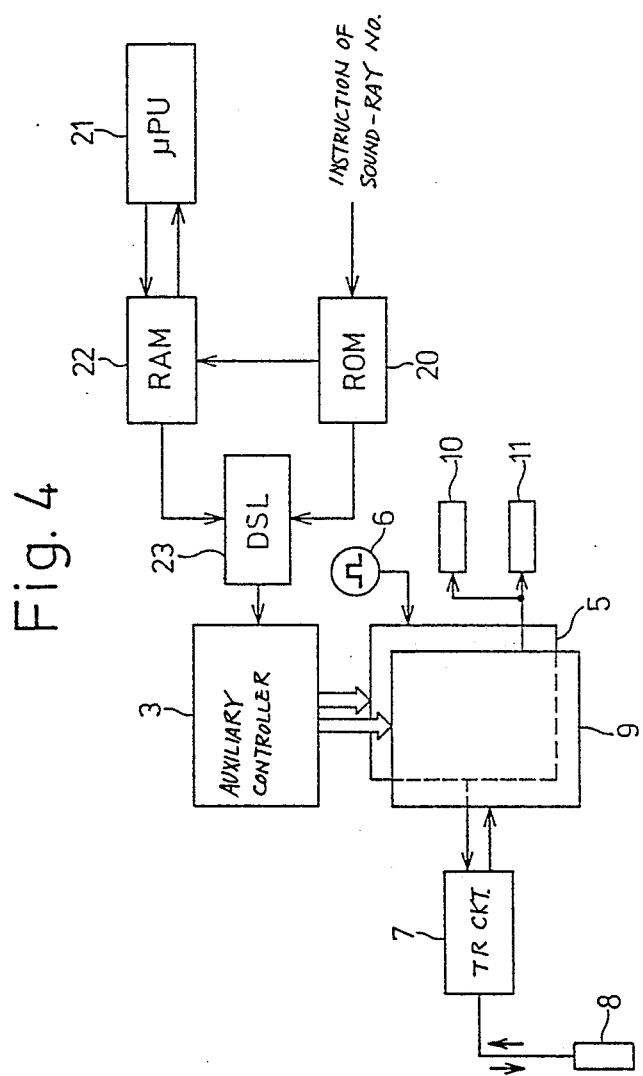
FIG. 4 is a block diagram according to another embodiment of the present invention.

In the case where a technique can be employed such that the ave surface is specified at each time when calculation is done, it is more excellent to perform blurring of the control data for a particular sound-ray under a desired condition rather than a method in which the array opening 13 is divided in a manner as described above and to each of which the control data of different sound-rays is applied. In the Doppler mode, unlike a real time B mode, it is not necessarY to change the sound-ray of the ultrasonic beam at every time but it is only necessary to rewrite the beam forming data whenever instruction is issued for altering the sample volume or for the movement. There is a time for performing this work, say about 100 msec, and within such a period of time it is possible to calculate the control data each time the instruction is issued and correct the same. FIG. 4 is a block diagram showing an embodiment in which the case as mentioned above is applied. In the figure, the same reference numerals are allotted to the same components as those shown in FIG. I Reference numeral 20 denotes a read-only memory (ROM) storing the beam forming data of the B mode sound-ray, 21 a microprocessor unit (μPU) for correcting the mode beam forming data, 22 random access memory (RAM) for storing data from the ROM 20 and the μPU 21, and 23 a data selector (DSL) for performing switchings between the data from the ROM 20 and RAM 22.

In this apparatus, at the time of B mode display operation, the beam forming data of &he B mode sound ray which has been stored in the ROM 20 is fed through the DSL 23 to the auxiliary controller 3. Other circuits in association with the auxiliary controller S are same in construction and operation as those shown in FIG. 1. On the other hand, at the time of D mode transmission, the beam forming data of the sound ray whose sound ray number has been designated by the ROM 20 is entered into the μPC 21 through the RAM 22, in which it is edited to provide beam forming data having a desired sample volume. The latter beam forming data is again sent to the RAM 22, and depending upon the timing of either the B mode or the D mode, the DSL 23 performs switchings and either the data extracted directly from the ROM 20 (B mode) or the edited data stored in the RAM 22 is inputted to the auxiliary controller 3.

Examples of the beam configurations produced by the apparatus according to the embodiment of the present invention are shown in FIGS. 5A through 5F. Those shown in FIGS. 5A and 5B are the B mode beam and the conventional D mode beam, respectively, in which the former is such that the dimension of the sample volume is small in both depth and width and the latter is such that the dimension is extended only in the depth direction by a range gate. FIGS. 5C through 5F are the diagrams illustrating sample volumes formed by enlarging the dimension further in &he direction of azimuth angle according to the embodiment of the present invention. FIGS. 5C and 5D show the cases Where enlargement is made only in the direction azimuth angle and no enlargement is made in the depth direction. FIGS. 5E and 5F show the cases where enlargements are made in both directions of the azimuth angle and the depth. The configurations of these beams are formed by the combination of the beam forming data for adjacent different sound-rays as in the embodiment shown in FIG. 1 or by the edition of the beam forming data by the μPU 21 as in the embodiment shown in FIG. 2. Provided that the formation of the beam is controlled in accordance with the width of the range gate, it becomes possible to interlockingly change the dimension of the sample volume both in the distance and azimuth angle directions. In this case, the burst length of the transmitting waveform may be varied to interlock therewith.

Although the present invention has been described with respect to a best mode for carrying out the invention, a variety of modifications may be made for a skilled artisan in the field of technology to which &he present invention pertains without departing from the scope of the invention defined in the appended claims.

I claim:

1. An ultrasonic diagnostic apparatus
for transmitting and receiving a plurality of ultrasonic beams in both a B-mode and a Doppler mode, comprising
a vibrator array means for transmitting and receiving the ultrasonic beams of selected beam width in azimuth direction and of selected beam depth in depth direction and having an opening divided into N parts;
means for producing beam forming data for adjacent ultrasonic beams, said data being divided into N parts for each adjacent ultrasonic beam; and
means for carrying out focusing in the Doppler mode by applying selected parts of the beam forming data of adjacent ultrasonic beams to respective parts of the vibrator array opening so that the beam width in the aximuth direction is increased.

2. The apparatus of claim 1, comprising means for editing the beam forming data so as to increase the depth of the beam.

3. An ultrasonic diagnostic apparatus for transmitting and receiving an ultrasonic beam in both a B-mode and a Doppler mode, comprising
a vibrator array means for transmitting and receiving ultrasonic beams of selected depth;
means for producing beam forming data for the ultrasonic beams in the B-mode and for the ultrasonic beams in the Doppler mode;
first memory means for storing the beam forming data for the B-mode;
second memory means for storing the beam forming data for the Doppler mode;
means for selectively applying beam forming data from the first and second memory means to the vibrator array in the B-mode or the Doppler mode; and
computer means for editing data from the second memory means to increase at least the depth of the beam, said editing being done during the time of the application of the Doppler mode, said computer means applying the edited beam forming data to the means for selectively applying when the beam depth is desired to be increased.

* * * * *